US00PP21335P2

(12) United States Plant Patent
Utecht

(10) Patent No.: US PP21,335 P2
(45) Date of Patent: Sep. 28, 2010

(54) ***PELARGONIUM* PLANT NAMED 'FISRUBITO'**

(50) Latin Name: ***Pelargonium peltatum* (L.)** *L'Hérit ex Ait*
Varietal Denomination: Fisrubito

(75) Inventor: Angelika Utecht, Montabaur (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/456,415

(22) Filed: Jun. 16, 2009

(51) Int. Cl.
*A01H 5/00* (2006.01)

(52) U.S. Cl. ..... Plt./332

(58) Field of Classification Search ..... Plt./332
See application file for complete search history.

*Primary Examiner*—Annette H Para

(74) *Attorney, Agent, or Firm*—S. Matthew Edwards

(57) ABSTRACT

A new *Pelargonium* plant named 'Fisrubito' particularly distinguished by the double- type, medium sized, dark-red flowers, floriferous with relatively small inflorescences, medium green foliage, leaves with distinct lobes and weak, narrow zonation, about medium vigor, initially ascending, later trailing, bushy and tight, about medium sized plant habit.

2 Drawing Sheets

Latin name of the genus and species of the plant claimed: *Pelargonium peltatum* (L.) *L'Hérit. ex Ait.*
Varietal denomination: 'Fisrubito'.

BACKGROUND OF THE NEW PLANT

The present invention comprises a new ivy *geranium* plant, botanically known as *Pelargonium peltatum* and hereinafter referred to by the variety name 'Fisrubito'.

'Fisrubito' is a product of a planned breeding program. The new cultivar has dark-red, double flowers, medium green foliage with weak zonation, and trailing, bushy, compact to medium sized plant habit.

'Fisrubito' originated from a hybridization made in the late summer of 2005 in a controlled breeding program in Hillscheid, Germany. The female parent was the commercial variety 'Maxime,' U.S. Plant Pat. No. 16,683 'Fismaxi'.'Fismaxi' has medium red, double flowers, medium green foliage with weak zonation, and about medium sized, bushy plant habit, while 'Fisrubito' has dark-red flower color.

The male parent of 'Fisrubito' was the commercial variety 'Ruby Dream,' U.S. Plant Pat. No. 17,813 'Fisruby'. 'Fisruby' has dark-red, double flowers, zoned foliage, and about medium to tall, trailing plant habit, while 'Fisrubito' has smaller flower and inflorescences, shorter peduncles, weaker leaf zone, and a shorter plant habit.

'Fisrubito' was selected as one flowering plant within the progeny of the stated cross in the spring of 2006 in a controlled environment in Galdar, Gran Canaria, Spain.

The first act of asexual reproduction of 'Fisrubito' was accomplished when vegetative cuttings were taken from the initial selection in the fall of 2006 in a controlled environment in Galdar, Gran Canaria, Spain.

Horticultural examination of plants grown from cuttings of the plant initiated in March 2007 in Hillscheid, Germany, and continuing thereafter, has demonstrated that the combination of characteristics as herein disclosed for 'Fisrubito' are firmly fixed and are retained through successive generations of asexual reproduction.

'Fisrubito' has not been observed under all possible environmental conditions. The phenotype may vary significantly with variations in environment such as temperature, light intensity and day length.

Plant Breeder's Rights for this cultivar were applied for in Switzerland on Jun. 23, 2008 and in Canada on Mar. 9, 2009. 'Fisrubito' has not been made publicly available more than one year prior to the filing of this application.

BRIEF DESCRIPTION OF THE PHOTOGRAPHS

The accompanying photographic drawings show typical flower and foliage characteristics of 'Fisrubito' with colors being as true as possible with an illustration of this type.

DETAILED BOTANICAL DESCRIPTION

Figure 1:
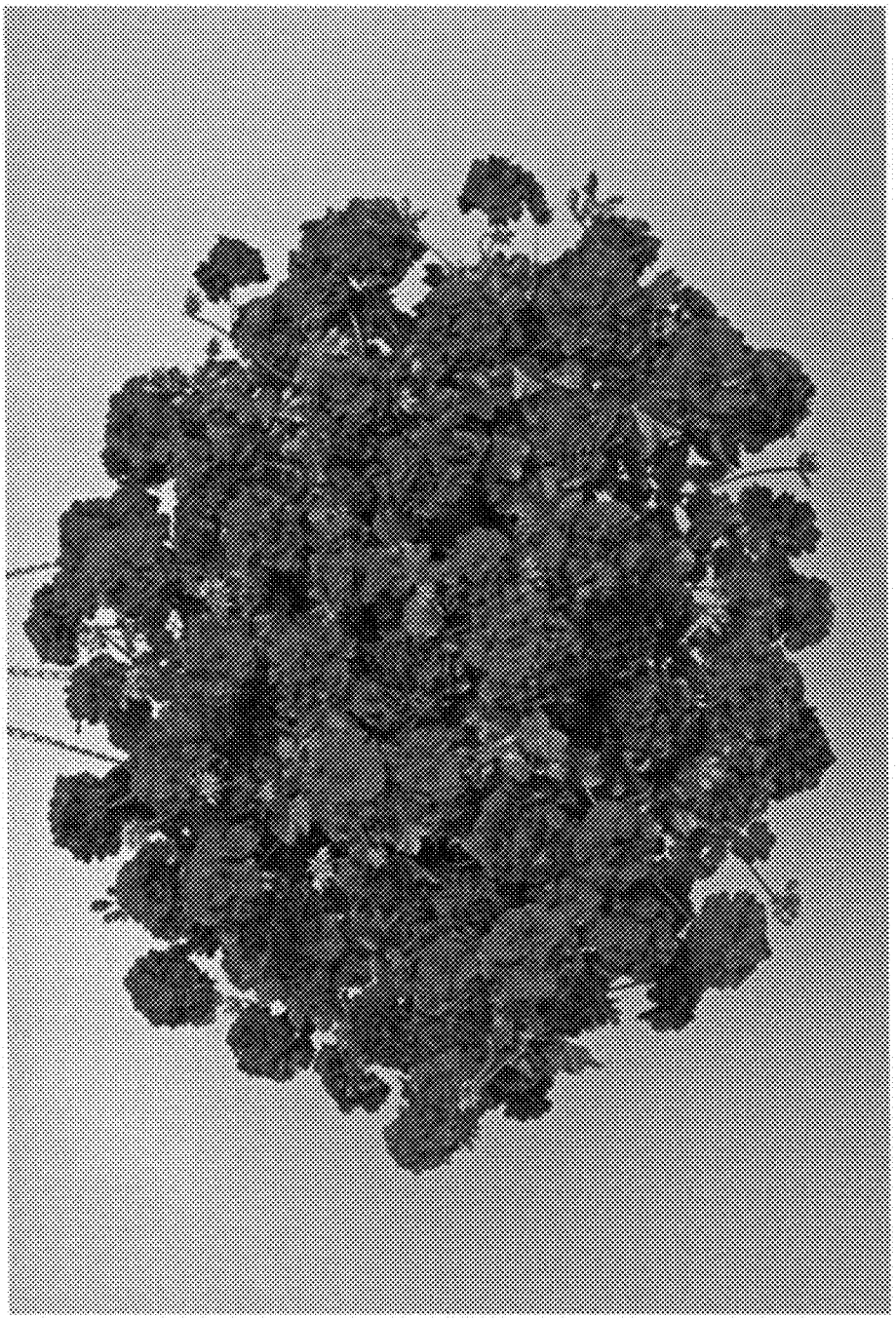
FIG. 1 shows a flowering hanging basket holding three about seven month old plants.
Figure 2:
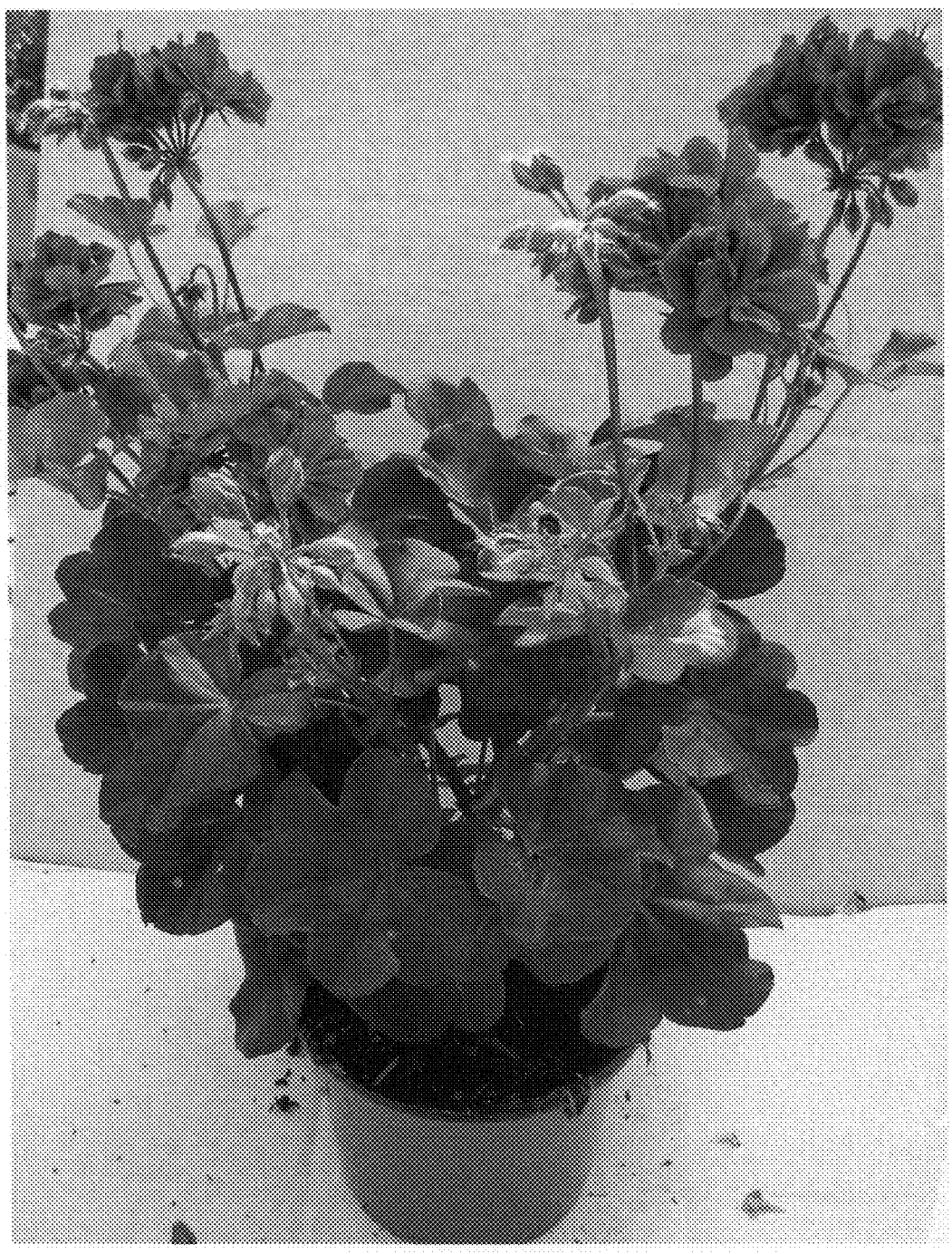
FIG. 2 shows a three month old potted plant of the new variety.

The measurements were taken in Hillscheid, Germany, on Apr. 29, 2009 on 12 week old plants that were growing in a greenhouse. Culture of these plants started in early February 2009, when rooted cuttings were planted into 12 cm pots, and were pinched once. Plants were grown out on benches at minimum day/night temperatures of only 14° /16° C. until April 1, and at higher temperatures thereafter.

Color Chart used: Royal Horticultural Society Colour Chart (R.H.S.) 2001.

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* (common name: ivy *geranium*) as a new and distinct variety.

1. Medium to large sized, double-type, deep-red colored flowers.
2. Numerous, relatively small, semi-spherically shaped umbels.
3. Flower heads borne at about medium distance above the foliage.
4. Medium green foliage, leaves with distinct lobes and with weak, narrow, ring-shaped zone.
5. initially relativley compact and spreading, later trailing, bushy, tight, about medium sized habit.
6. Early flowering, and floriferous throughout the summer.

DIFFERENCES BETWEEN THE NEW VARIETY 'FISRUBITO' AND SIMILAR VARIETIES:

In comparison to the parent variety 'Fisruby,' U.S. Plant Pat. No.17,813, 'Fisrubito' has a roughly similar flower color, but smaller flowers, distinctly smaller inflorescences, shorter peduncles, a narrower leaf zone, and a more compact habit with shorter branches.

In comparison to 'Free Rured,' U.S. Plant Pat. No. 18,042, 'Fisrubito' has a slightly deeper red overall flower color, fewer petals, deeper green foliage color, and a different leaf shape with more distinct leaves.

In comparison with 'Fisbildeep' (U.S. Plant Pat. 20,592), 'Fisrubito' has slightly larger and differently shaped flowers, no rose-bud shape, fewer petals (15-20 petals, in contrast to 25-30 for 'Fisbildeep'), narrower and slightly weaker leaf zone, tighter plant habit, and earlier flowering.

Plant:

*Form, growth and habit.*—Initially semi-upright, later trailing.

*Plant height.*—16.5 cm.

*Plant height* (*inflorescence included*).—19-21 cm.

*Plant diameter.*—24.8 cm.

*Plant size at the end of the summer, About* 6 months old, plant spread from the base of the main stem to the shoot tips.—50-60 cm.

*Number of branches.*—8-10.

Stem:

*Color of stem.*—Green, RHS 143C, no anthocyanin.

*Length of stem.*—About 14-17 cm.

*Diameter.*—4-5 mm at middle portion.

*Length of internodes.*—1-4 cm.

*Texture.*—Covered with fine short hair.

Foliage:

*Immature leaf, color upper surface.*—RHS 137D.

*Immature leaf, lower surface.*—Between RHS 143B and 138A.

*Mature leaf, color upper surface.*—Medium green, RHS 137B to 137C.

*Mature leaf, color lower surface.*—RHS 143B.

*Length.*—4.8-5.3 cm.

*Width.*—8.3 cm.

*Shape.*—Ivy shaped with distinct, rounded lobes.

*Base shape.*—Cordate, gap between lowest lobes closed or nearly closed.

*Apex shape.*—Rounded lobes.

*Margin.*—Entire, partly crenated at the tips.

*Texture.*—Leathery, appears glabrous, but upper side covered with very fine, short hair, apart from that, hair along the edges (hirtellous) and the veins of the underside.

*Leaf zone.*—Narrow ring, weak, color brown, RHS 147A or 166A.

*Color of veins, upper surface.*—Indistinct, approximately RHS 144A.

*Color of veins, lower surface.*—Light green, RHS.

*Petiole color.*—RHS 137D.

*Petiole length.*—Most often between 3-4.5 cm.

*Diameter of petiole.*—2 mm.

*Texture.*—Very short, fine hair.

Inflorescence:

*Begin of flowering.*—(50% of plants on April 20, 10-11 weeks old with open flowers).

*Duration of flowering.*—Continuous flowering throughout the Summer.

*Type and shape of inflorescence.*—Umbel, semi-spherical, tight, small to medium sized.

*Number of inflorescences per plant.*—4-5 at the stated time, approx. 20-25 in late summer.

*Number of flowers and buds per inflorescence.*—Most often 10-15.

*Umbel diameter.*—7.8 cm.

*Umbel depth.*—4.0-5.0 cm.

Peduncle:

*Color of peduncle.*—Green, RHS 143A to 143B.

*Length of peduncle.*—10.8 cm.

*Peduncle diameter.*—3 mm.

*Texture.*—Covered with sparse fine hair.

Pedicel:

*Color of pedicel.*—Green, RHS 146A, may be weakly infused with anthocyanin (brown color).

*Length of pedicel.*—1.9 cm.

*Diameter of pedicel.*—1.5 mm.

*Texture.*—Pubescent.

Corolla:

*Form.*—Double-type, nearly round, with the petals upwards and outwards directed.

*Diameter of flower.*—4.7 cm.

*Depth of flower.*—1.5-2.0 cm.

*Number of petals.*—Approximately 15-20.

*Color upper petals, upper surface.*—RHS 46A, partly overlain with a blackish shimmer, near RHS 187A, at the base very dark veins, between RHS 187A and RHS 202A.

*Color upper petals, lower surface.*—Deep red, between RHS 53B and RHS 61B.

*Length of upper petals.*—24-27 mm.

*Width of upper petals.*—13-18 mm.

*Color lower petals, upper surface.*—Between RHS 46A and 46B.

*Color lower petals, lower surface.*—Deep red, between RHS 46B and 53B.

*Length of lower petals.*—23-25 mm.

*Width of lower petals.*—15-17 mm.

*Petal shape.*—Mostly obovate, upper petals obovate to spatulate.

*Apex shape.*—Rounded.

*Margin.*—Entire.

*Base.*—Acute.

*Petal texture.*—Smooth, glabrous.

*Number of petaloids.*—0 to 2, narrower and shorter than petals.

*Color of petaloids.*—Similar as petals, or of somewhat less intense hue.

Bud (just before opening):

*Color.*—Purple, more reddish hue than RHS 61B.

*Length.*—19-21 mm.

*Width.*—10-13 mm.

*Shape.*—Elliptical.

Calyx:

*Number of sepals.*—Usually 5, occasionally 6.

*Color of sepals.*—Grass-green, abaxial green, RHS 143B to 143C, adaxial RHS 143C, no anthocyanin.

*Length of sepals.*—14-16 mm.

*Width of sepals.*—5-6 mm for the largest sepal, 3 mm for the other sepals.

*Sepal shape.*—Lanceolate.

*Apex shape.*—Acute to acuminate.

*Margins.*—Entire.

*Texture.*—Covered with a few relatively long, soft hairs.

Reproductive organs gynoecium:

*Pistil.*—One.

*Length.*—10-12 mm.

*Style color.*—Whitish to pale pink, RHS 69C.

*Style length.*—3-4 mm.

*Stigma color.*—Purple, near, RHS 61A.

Androecium:

*Number of anthers.*—None or up to 3.

*Length of anthers.*—2 mm.

*Anther color.*—Dark purple, RHS 187A.

*Length filaments.*—7-9 mm.

*Color of filaments.*—White to pale pink, RHS 68B, at upper end.

*Pollen amount.*—Relatively little per flower.

*Color of pollen.*—Orange, RHS 25A.

Fertility:

*Seed set.*—No seed set observed.

Disease/pest resistance: Disease resistance or susceptibility has not been observed on this hybrid.

What is claimed is:

1. A new and distinct variety of *Pelargonium* plant named 'Fisrubito' substantially as illustrated and described herein.

* * * * *

UNITED STATES PATENT AND TRADEMARK OFFICE

CERTIFICATE OF CORRECTION

PATENT NO. : PP 21,335 P2
APPLICATION NO. : 12/456415
DATED : September 28, 2010
INVENTOR(S) : Utecht It is certified that error appears in the above-identified patent and that said Letters Patent is hereby corrected as shown below:

At (57), in the ABSTRACT, delete "double- type" and insert therefor --double-type--

At column 1, line 25, delete "flower" and insert therefor --flowers--

At column 3, line 11, delete "relativley" and insert therefor --relatively--

At column 3, line 26, delete "leaves" and insert therefor --lobes--

At column 4, line 5, delete "Light green, RHS." and insert therefor --RHS 145A--

Signed and Sealed this

Thirtieth Day of November, 2010

David J. Kappos

David J. Kappos
*Director of the United States Patent and Trademark Office*